US008852567B2

(12) United States Patent
Bui et al.

(10) Patent No.: US 8,852,567 B2
(45) Date of Patent: *Oct. 7, 2014

(54) STABLE COMPOSITIONS OF VARYING VISCOELASTICITY

(75) Inventors: Hy Si Bui, Piscataway, NJ (US); Mohamed Kanji, Edison, NJ (US); Susan Halpern, Paramus, NJ (US); Ella Rapoport, Morganville, NJ (US)

(73) Assignee: L'Oreal, Paris (FR)

( * ) Notice: Subject to any disclaimer, the term of this patent is extended or adjusted under 35 U.S.C. 154(b) by 215 days.

This patent is subject to a terminal disclaimer.

(21) Appl. No.: 13/133,179

(22) PCT Filed: Dec. 9, 2009

(86) PCT No.: PCT/US2009/067342
§ 371 (c)(1),
(2), (4) Date: Aug. 2, 2011

(87) PCT Pub. No.: WO2010/077745
PCT Pub. Date: Jul. 8, 2010

(65) Prior Publication Data
US 2011/0286949 A1 Nov. 24, 2011

Related U.S. Application Data

(60) Provisional application No. 61/120,885, filed on Dec. 9, 2008, provisional application No. 61/120,877, filed on Dec. 9, 2008, provisional application No. 61/120,876, filed on Dec. 9, 2008.

(51) Int. Cl.
| | | |
|---|---|---|
| *A61Q 1/12* | (2006.01) | |
| *A61K 8/84* | (2006.01) | |
| *A61Q 1/10* | (2006.01) | |
| *A61K 8/31* | (2006.01) | |
| *A61K 8/04* | (2006.01) | |
| *A61K 8/37* | (2006.01) | |
| *A61Q 1/04* | (2006.01) | |
| *A61K 8/81* | (2006.01) | |

(52) U.S. Cl.
CPC ... *A61K 8/84* (2013.01); *A61Q 1/10* (2013.01); *A61K 8/31* (2013.01); *A61K 8/042* (2013.01); *A61K 8/37* (2013.01); *A61Q 1/04* (2013.01); *A61K 8/8111* (2013.01); *A61K 8/8164* (2013.01)
USPC ........................................ 424/78.02; 424/401

(58) Field of Classification Search
None
See application file for complete search history.

(56) References Cited

U.S. PATENT DOCUMENTS

| | | | | |
|---|---|---|---|---|
| 4,871,536 | A | * | 10/1989 | Arraudeau et al. ............. 424/59 |
| 5,063,052 | A | * | 11/1991 | Grollier et al. ........... 424/70.121 |
| 5,389,363 | A | | 2/1995 | Snyder et al. |
| 5,800,816 | A | | 9/1998 | Brieva et al. |
| 5,911,974 | A | | 6/1999 | Brieva et al. |
| 5,965,112 | A | | 10/1999 | Brieva et al. |
| 5,985,298 | A | | 11/1999 | Brieva et al. |
| 6,274,152 | B1 | | 8/2001 | Brieva et al. |
| 6,464,964 | B1 | | 10/2002 | Brieva et al. |
| 6,482,400 | B1 | | 11/2002 | Collin |
| 6,562,322 | B2 | | 5/2003 | Brieva et al. |
| 6,780,422 | B2 | | 8/2004 | Brieva et al. |
| 7,005,134 | B2 | | 2/2006 | Brieva et al. |
| 7,160,550 | B2 | | 1/2007 | Brieva et al. |
| 2003/0147931 | A1 | | 8/2003 | Brieva et al. |
| 2005/0276763 | A1 | * | 12/2005 | Pfeifer et al. .................. 424/59 |
| 2006/0159642 | A1 | | 7/2006 | Hanna et al. |
| 2007/0092468 | A1 | | 4/2007 | Brieva et al. |
| 2007/0110690 | A1 | * | 5/2007 | Nguyen et al. ............... 424/70.1 |

OTHER PUBLICATIONS

U.S. Appl. No. 13/133,187, filed Aug. 31, 2011, Bui, et al.
U.S. Appl. No. 13/132,724, filed Aug. 11, 2011, Bui, et al.
U.S. Appl. No. 13/132,811, filed Jul. 29, 2011, Bui, et al.
U.S. Appl. No. 13/140,083, filed Aug. 17, 2011, Bui, et al.
International Search Report issued Jun. 28, 2010 in PCT/US09/67342 filed Dec. 9, 2009.

* cited by examiner

*Primary Examiner* — Jyothsna Venkat
(74) *Attorney, Agent, or Firm* — Oblon, Spivak, McClelland, Maier & Neustadt, L.L.P.

(57) ABSTRACT

The present invention is directed to cosmetic compositions having an unique texture and feel containing: (a) at least one polyamine; (b) at least one oil-soluble polar modified polymer; (c) water; (d) optionally, at least one volatile solvent, other than water; (e) at least one non-volatile oil capable of solubilizing the oil-soluble polar modified polymer; and (f) optionally, at least one colorant.

3 Claims, 1 Drawing Sheet

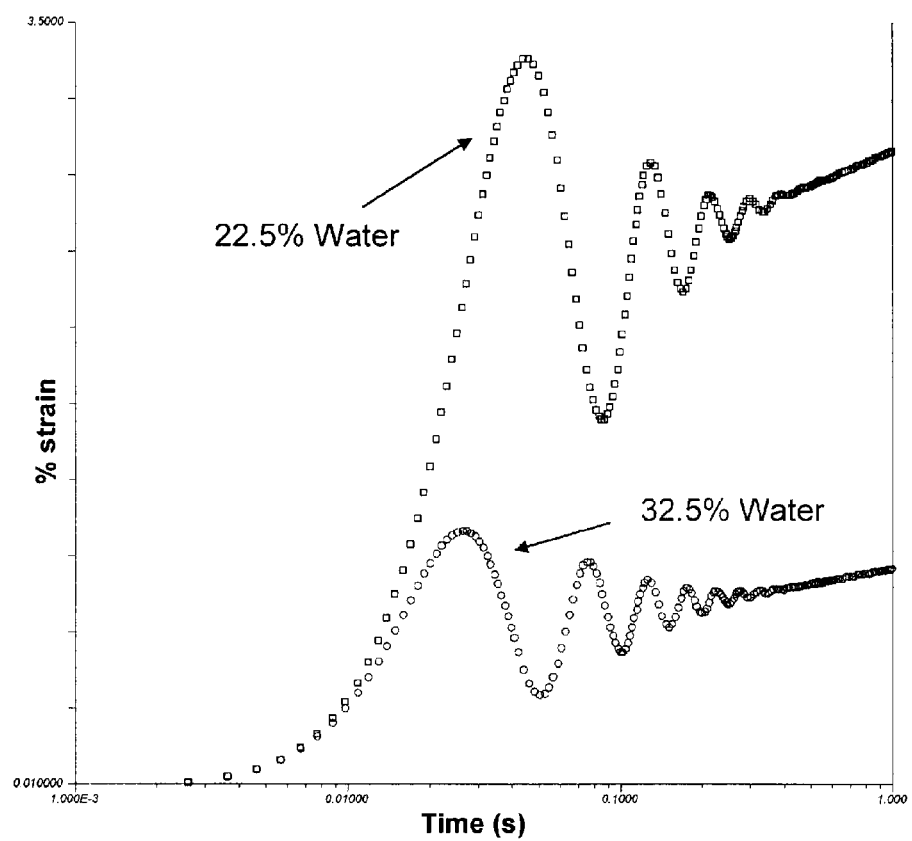
Effect of water on Instantaneous Creep Strain Oscillation at Constant Stress = 10Pa for Examples 1 and 2

STABLE COMPOSITIONS OF VARYING VISCOELASTICITY

FIELD OF THE INVENTION

The present invention generally relates to a novel composition capable of possessing varying degrees of viscoelasticity. More particularly, the present invention relates to a composition that can possess a broad spectrum of textures and feel ranging from liquid to rigid gel.

DISCUSSION OF THE BACKGROUND

Many compositions, especially cosmetic compositions, have been developed for easy and comfortable application onto a targeted substrate. Unfortunately, many of these compositions are in fact difficult to apply and do not possess a smooth feel upon application. Moreover, compositions oftentimes have a tendency to feel tacky, yielding poor application and spreadability characteristics.

In general, a gel-like texture is typically obtained with the use of expensive silicone elastomers which are swelled in a solvent. The present invention does not require the use of silicone elastomers in order to achieve the desired gel-like texture. Moreover, silicone elastomers can also be difficult to formulate with due to their chemical make up, and the gelled compositions they form may be unstable, as is, or sensitive to added ingredients.

Similarly, a rigid texture is typically obtained through the use of waxes and wax-like ingredients. The present invention, however, does not require the use of these types of conventionally-employed ingredients in order formulate compositions having a rigid texture. On the contrary, essentially the same ingredients used to formulate a composition having a gel-like texture can be used to formulate one having a rigid texture. Significant cost reductions are thus realized due to the relatively inexpensive cost of the ingredients used, as well as the ease in formulating such compositions.

Therefore, it is an object of the present invention to provide a composition capable of possessing a texture and feel ranging from liquid to rigid gel, without the need for having to use expensive ingredients and/or processing techniques, and which can serve as a stable base/matrix for the incorporation of various types of ingredients.

SUMMARY OF THE INVENTION

The present invention relates to a composition containing:
(a) at least one polyamine;
(b) at least one oil-soluble polar modified polymer;
(c) water;
(d) at least one non-volatile oil capable of solubilizing the oil-soluble polar modified polymer;
(e) optionally at least one volatile solvent other than water; and
(f) optionally, at least one colorant.

The present invention also relates to a composition containing:
(a) a reaction product of at least one polyamine and at least one oil-soluble polar modified polymer;
(b) water;
(c) at least one non-volatile oil capable of solubilizing the oil-soluble polar modified polymer;
(d) optionally at least one volatile solvent other than water; and
(e) optionally, at least one colorant.

The present invention relates to a composition made by combining ingredients comprising:
(a) at least one polyamine;
(b) at least one oil-soluble polar modified polymer;
(c) water;
(c) at least one non-volatile oil capable of solubilizing the oil-soluble polar modified polymer;
(d) optionally at least one volatile solvent other than water; and
(e) optionally, at least one colorant.

Preferably, the composition does not require or contain silicone elastomers.

The present invention also relates to methods of making up keratinous substrates involving applying the above-disclosed composition onto the substrates.

It has been surprisingly been discovered that depending on the amount of volatile solvent capable of forming a hydrogen bond with the polyamine/oil-soluble polar modified polymer, present in the above-disclosed composition, the texture and feel of the composition can range from liquid to rigid gel, in the absence of expensive ingredients and/or processing techniques, and in a more environmentally-friendly manner.

It has also been surprisingly been discovered that depending on the crosslink density of the composition, which is controlled by varying the amounts of polyamine and oil-soluble polar modified polymer present in the composition, the texture and feel of the composition can range from liquid to rigid gel, in the absence of expensive ingredients such as silicone elastomers, silicone resins, emulsifiers or gelling agents and/or processing techniques, and in a more environmentally-friendly manner.

It has also been surprisingly discovered that in the absence of silicone resins and traditional film formers, that the resultant product is eminently capable of forming a film with highly transfer resistant and long wearing properties.

The resultant composition can be used as a stable matrix for carrying desirable ingredients to be applied in a comfortable, smooth, and easily spreadable manner.

BRIEF DESCRIPTION OF THE DRAWINGS

FIG. 1 is a graph representing the effect of water on Instantaneous Creep Strain Oscillation at Constant Stress=10 Pa for Examples 1 and 2.

DETAILED DESCRIPTION OF THE INVENTION

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. Nos. 5,530,092 and 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.1 to about 10% by weight, more preferably from about 0.2 to about 5% by weight, based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, $C_2$-$C_{20}$ compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are $C_2$-$C_8$ compounds, more preferably $C_2$-$C_6$ compounds, and most preferably $C_2$-$C_4$ compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP). According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; prop Point, Mettler: 106° C.) from Honeywell, A-C 596 A (PROPYLENE-MALEIC ANHYDRIDE COPOLYMER; prop Point, Mettler: 143° C.) from Honeywell, A-C 597 (PROPYLENE-MALEIC ANHYDRIDE COPOLYMER; prop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the polar modified polymer(s) represent from about 1% to about 30% of the total weight of the composition, more preferably from about 3% to about 20% of the total weight of the composition, and most preferably from about 5% to about 15%, including all ranges and subranges therebetween.

Water

The composition of the present invention also contains water. Preferably, water is present in an amount sufficient to solubilize the polyamine present in the composition. The water is typically employed in an amount of from about 0.05% to about 50% by weight, such as from about 0.05% to about 10% by weight, such as 1% to 8% and 2% to 5% by weight, and from about 1% to about 40% by weight, such as from about 2% to about 30% by weight, including all ranges and subranges therebetween, all weights being based on the total weight of the composition.

Volatile Solvents Other than Water

The compositions of the present invention can include at least one volatile solvent other than water. The volatile solvent is preferably chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96β of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In general, the at least one volatile solvent is present in the composition in an amount of from about 20 to about 90% by weight, such as from about 30 to about 80% by weight, and from about 35 to about 75% by weight, including all ranges and subranges therebetween, all weights being based on the total weight of the composition.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

Similarly, while not wanting to be bound by theory, it is also believed that the composition can range from liquid to rigid gel is due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof, water-washable and inherently possesses the desired cushiony/bouncy texture and feel. Moreover, the product is both stable and capable of carrying various types of ingredients.

Non-Volatile Solvent

The cosmetic compositions of the present invention comprise at least one non-volatile solvent capable of solubilizing the oil-soluble polar modified polymer. As used herein, the term "non-volatile" means having a flash point of greater than about 100° C. The at least one non-volatile solvent typically comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_{7\geq10}$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

Further, examples of hydrocarbon oils which may be used include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The at least one non-volatile solvent is preferably present in the cosmetic composition of the invention in an amount of from about 1% to about 95% by weight, such as from about 1.5% to about 10% by weight, such as from about 2% to about 5% by weight, and such as from about 30% to about 80% by weight, such as from about 40% to about 70% by weight, including all ranges and subranges therebetween, all weights being based on the total weight of the composition.

Optional Ingredients

The composition of the present invention may also include any one, or more, optional ingredients. Examples thereof include, but are not limited to, colorants such as dyes and pigments, co-solvents (volatile and/or non-volatile), waxes, plasticizers, preservatives, fillers, active ingredients such as those used to treat skin and hair and sunscreens.

It has surprisingly been discovered that the composition of the present invention, in order to be effective as a base/matrix for carrying insoluble ingredients, does not require the use of silicone resins, emulsifiers or gelling agents. Accordingly, according to preferred embodiments of the present invention, the compositions of the present invention are free of any combination of silicone resins, emulsifiers, surfactants and/or gelling agents.

The compositions of the present invention possess a texture and feel ranging from liquid to rigid gel, depending on the amount of water present in the composition and/or temperature at which the oil-soluble polar modified polymer and polyamine are reacted.

The composition of the present invention possess a texture and feel ranging from liquid to rigid gel, depending on either the crosslink density of the composition which, as was indicated above, can be varied depending on the amounts of polyamine and oil-soluble polar modified polymer present in the composition or the temperature at which the reaction product is formed.

The cushiness/bounciness of the composition is characterized by its "instantaneous creep strain oscillation" which is determined over a short interval of deformation of the material or composition during a creep experiment.

Instantaneous creep strain oscillation, over a short interval of deformation, is determined by measuring the response of the composition or material to an applied stress over a period of time of less than or equal to 1 second (t≤1 second) such as, for example, from 0.001 second to 1 second. The composition or material will show some strain damping oscillations if the material is a cushiony/bouncy liquid or gel or solid, as is seen in FIG. 1.

Similarly, the elasticity or hardness or softness of the composition or material is characterized by its "creep recoverable compliance" which is determined after a longer interval of creep deformation of the composition or material during a creep and recovery experiment.

In the event that the composition contains a low amount of water, the composition will have a soft feel and be very cushiony/bouncy. This phenomenon is evidenced by the instantaneous creep strain oscillation where a higher strain amplitude and damp, with smaller numbers of oscillation, are observed as compared to a material which contains larger amounts of water and, consequently, a harder feel. For a more bouncy and cushiony composition, the maximum amplitude strain of the first instantaneous oscillating peak should be larger than that of the less bouncy and less cushiony composition.

In the event the composition contains less than about 25% by weight, based on the weight of the composition, of water, it will possess a creep recoverable compliance R(trecovery) of $5\times10^{-3}$ to 1.0 1/Pa, and a maximum instantaneous creep strain oscillation of about 2-50%, which translates into the material having a higher degree of cushioniness/bounciness, i.e. softer feel and texture. Conversely, if the composition contains greater than about 25% by weight, based on the weight of the composition, of water, it will possess a creep recoverable compliance of $1\times10^{-5}$ to $5\times10^{-3}$ 1/Pa, and a maximum instantaneous creep strain oscillation of 0.1-2.0%, which translates into the material having a lower degree of cushioniness/bounciness, i.e. harder feel and texture.

In the event that the composition contains less than about 10% of the oil-soluble polar modified polymer and less than about 2% of the polyamine the composition will have a soft feel and cushiony/bouncy texture due to a low crosslink density. This phenomenon is evidenced by the instantaneous creep strain oscillation where a higher strain amplitude and damp, with smaller numbers of oscillation. Thus, for those compositions in which the texture is more bouncy/cushiony, the maximum amplitude strain of the first instantaneous oscillating peak should be larger than that of the less bouncy/cushiony composition.

In the event that the composition contains more than about 10% of the oil-soluble polar modified polymer and more than about 2% of the polyamine the composition will have a harder feel and less of a cushiony/bouncy texture due to a higher crosslink density. This phenomenon is evidenced by the instantaneous creep strain oscillation where a lower strain amplitude and damp, with higher numbers of oscillation. Thus, for a less bouncy/cushiony composition, the maximum amplitude strain of the first instantaneous oscillating peak should be smaller than that of the more bouncy/cushiony composition.

The composition of the present invention will possess, depending on the respective amounts of polyamine and oil-soluble polar modified polymer present in the composition, a creep recoverable compliance R($t_{recovery}$=20 minutes) at a constant stress of 10 Pa of from about $10^{-4}$ to about $10^{-1}$ 1/Pa, and a maximum instantaneous creep strain oscillation of from about 0.1% to about 50%. Varying degrees of rigidity of the material, i.e., from liquid to rigid gel, are achieved by varying the amounts of polyamine and oil-soluble polar modified polymer in the composition.

As was noted above, the elasticity or hardness or softness of the composition or material is characterized by its "creep recoverable compliance" which is determined after a longer interval of creep deformation of the composition or material during a creep and recovery experiment. The creep recoverable compliance R($t_{recovery}$) will indicate the elastic response or softness or hardness of the material or composition.

Creep Experiments

The instantaneous creep strain oscillation, creep compliance and recovery compliance are determined by using a controlled stress rheometer, commercially available from TA Instruments under the name AR-G2. The samples are measured using a parallel plate having a stainless steel, cross hatched, 40 mm diameter plate. The gap is set at 1,000 microns. The desired temperature is precisely controlled by a Peltier system.

The sample is transferred to the rheometer, and held at 25° C. The sample is measured in the creep mode at a constant stress $\sigma_0$ of 10.0 Pa, at which the creep compliance J(t) is defined as:

$$J(t) = \frac{\gamma(t)}{\sigma_0}$$

Where γ(t) is the creep strain for a creep duration time t under a constant stress $\sigma_0$.

After creeping the sample for a duration of 10 minutes, the creep recoverable compliance R($t_{recovery}$) is observed for $t_{recovery}$=20 minutes at which the stress $\sigma_0$=0.

The composition of the present invention may be used for any application in which it is desirable to employ a waterproof film, capable of carrying insoluble ingredients such as, for example, pigments, and which is stable, easily spreadable, and comfortable to apply.

The present invention is further described in terms of the following non-limiting examples. Unless otherwise indicated, all parts and percentages are on a weight-by-weight percentage basis.

EXAMPLES 1 AND 2

|  | Contains water | |
|---|---|---|
| INCI | Example 1 % | Example 2 |
| HYDROGENATED POLYDECENE | 25.7 | 20.7 |
| OCTYLDODECYL NEOPENTANOATE | 25.7 | 20.7 |
| Isohexadecane | 2.6 | 2.6 |
| PP207 (*) | 8 | 8 |
| Lupasol G 35 PEI (PolyEthyleneImine) (50% SOLID/50% WATER) | 5 | 5 |
| TITANIUM DIOXIDE | 7.82 | 7.82 |
| IRON OXIDES | 1.46 | 1.46 |
| IRON OXIDES | 0.52 | 0.52 |
| IRON OXIDES | 0.2 | 0.2 |
| Isododecane | 3 | 3 |
| WATER | 20 | 30 |
|  | 100 | 100 |

(*) PP207 is a linear polypropylene-ethylene-maleic anhydride copolymer wax commercially available from Clariant under the tradename LICOCARE PP207 LP 3349.

Example 1 is a soft bouncy creamy gel
Example 2 is a hard bouncy creamy gel
Procedure for Examples 1 & 2

In container A, PP207 was melted in the isohexadecane, hydrogenated polydecene and the octyldodecyl neopentanoate until fully dissolved. The temperature was brought to 90° C.

While maintaining the temperature, the pigment grind were added to container A until fully dissolved.

In separate container B, LUPASOL G 35 PEI (PolyEthyleneImine) and water were mixed at room temperature;

B was added to A dropwise with a pipet at high sheer (~700 rpm);

Heat was maintained at 70° C.-80° C. for 20 minutes while maintaining high sheer mixing;

The mixture was cooled to room temperature while mixing.

CHART 1: Viscoelastic data for Examples 1-2

| EXAMPLE 1 contains 22.5% water | Stress = 10 Pa |
|---|---|
| Instantaneous Max Strain (%) | 3.33 |
| R(trecovery = 20 min) (1/Pa) | 6.52E−03 |

| EXAMPLE 2 contains 32.5% water | Stress = 10 Pa |
|---|---|
| Instantaneous Max Strain (%) | 1.17 |
| R(trecovery = 20 min) (1/Pa) | 2.25E−03 |

|  | Contains little water | |
|---|---|---|
| INCI | Example 3 | Example 4 |
| HYDROGENATED POLYDECENE | 30 | 27.5 |
| OCTYLDODECYL NEOPENTANOATE | 30 | 27.5 |
| Isohexadecane | 12.8 | 12.8 |
| PP207 (*) | 4.2 | 4.2 |
| Lupasol G 35 PEI (PolyEthyleneImine) (50% SOLID/50% WATER) | 10 | 5 |
| TITANIUM DIOXIDE | 7.82 | 7.82 |
| IRON OXIDES | 1.46 | 1.46 |
| IRON OXIDES | 0.52 | 0.52 |
| IRON OXIDES | 0.2 | 0.2 |
| Isododecane | 3 | 3 |
|  | 100 | 100 |

(*) PP207 is a linear polypropylene-ethylene-maleic anhydride copolymer wax commercially available from Clariant under the tradename LICOCARE PP207 LP 3349.

Example 3 and 4 are both soft gels

PROCEDURE FOR EXAMPLES 3-4

In container A, PP207 was melted in the isohexadecane, hydrogenated polydecene and the octyldodecyl neopentanoate until fully dissolved. The temperature was brought to 90° C.

While maintaining the temperature, the pigment grind were added to container A until fully dissolved.

LUPASOL G 35 PEI (PolyEthyleneImine) was added to A dropwise with a pipet at high sheer (~700 rpm);

Heat was maintained at 70° C.-80° C. for 20 minutes while maintaining high sheer mixing;

The mixture was cooled to room temperature while mixing.

Viscoelastic Data for Example 3 and 4

| Stress = 10 Pa | EXAMPLE 3 | EXAMPLE 4 |
|---|---|---|
| Instantaneous Max Strain (%) | 4.44 | N/A |
| R(trecovery = 20 min) (1/Pa) | $9.24 \times 10^{-3}$ | 0.113 |

Transfer Resistant Formulations

| INCI | Example 5 % | Example 6 % | Example 7 % |
|---|---|---|---|
| ISODODECANE | 72.5 | 55.5 | 53.75 |
| ISOHEXADECANE | 2.5 | 2.5 | 1.95 |
| PP207* | 7.5 | 7.5 | 6.5 |
| WATER | 0 | 17 | 20.5 |
| PEI-35 (50% water) | 10 | 10 | 4 |
| POTASSIUM CETYL PHOSPHATE | 0 | 0 | 3 |
| SIMETHICONE | 0 | 0 | 0.3 |
| TITANIUM DIOXIDE (and) DISODIUM STEAROYL GLUTAMATE (and) ALUMINUM HYDROXIDE | 7.82 | 7.82 | 7.82 |
| IRON OXIDES (and) DISODIUM STEAROYL GLUTAMATE (and) ALUMINUM HYDROXIDE | 1.46 | 1.46 | 1.46 |

-continued

| INCI | Example 5 % | Example 6 % | Example 7 % |
|---|---|---|---|
| IRON OXIDES (and) DISODIUM STEAROYL GLUTAMATE (and) ALUMINUM HYDROXIDE | 0.52 | 0.52 | 0.53 |
| IRON OXIDES (and) DISODIUM STEAROYL GLUTAMATE (and) ALUMINUM HYDROXIDE | 0.2 | 0.2 | 0.19 |

(*) PP207 is a linear polypropylene-ethylene-maleic anhydride copolymer wax commercially available from Clariant under the tradename LICOCARE PP207 LP 3349.

Example 5 is a highly transfer resistant liquid
Example 6 is a highly transfer resistant soft creamy gel
Example 7 is a transfer proof bouncy gel
Procedure for Examples 5-7
In container A, PP207 was melted in the isohexadecane and isododecane until fully dissolved. The temperature was brought to 90° C.
While maintaining the temperature, the pigment grind were added to container A until fully dissolved.
In separate container B, LUPASOL G 35 PEI (PolyEthyleneImine) and water were mixed at room temperature;
B was added to A dropwise with a pipet at high sheer (~700 rpm);
Heat was maintained at 70° C.-80° C. for 20 minutes while maintaining high sheer mixing;
The mixture was cooled to room temperature while mixing.
Transfer Resistant Data
Example 7 above was tested for transfer resistance following the expert panel methodology for testing. The panelists all have a piece of cloth that is 18"×6.5" and clips it into the shape of a turtleneck that measures 16" by 6.5". Panelist spreads 0.1 ml of foundation on face and waits 10 minutes. After 10 minutes, panelist pulls cloth headband up their face and removes headband. Panelist then grades cloth for amount of transfer.
Results
Following the expert panel method, this formulation has higher transfer resistant properties (transfer proof) than other top long wearing, transfer resistant formulas on the market.

What is claimed is:

1. A composition comprising:
   (a) a branched polyalkyleneimine in an amount of 0.05 to 10% by weight, based on the weight of the composition;
   (b) a linear polypropylene/polyethylene/maleic anhydride copolymer wax in an amount of 3 to 20% by weight, based on the weight of the composition;
   (c) water in an amount of from 15% to 35% by weight of the composition;
   (d) from about 1 to about 95% by weight, based on the weight of the composition, a non-volatile solvent capable of solubilizing the linear polypropylene/polyethylene/maleic anhydride copolymer wax and wherein the non-volatile solvent is a non-volatile oil,
   (e) a volatile solvent selected from isododecane and isohexadecane in an amount of about 30 to 80% by weight of the composition, and
   (f) a colorant,
   wherein the composition is free of silicone elastomer, silicone resin, synthetic film former, emulsifier and gelling agent.

2. The composition of claim 1, wherein the composition has a creep recoverable compliance of from $10^{-4}$ to $10^{-1}$ (1/Pa), and a maximum instantaneous creep strain oscillation of from 0.1 to 50% at a constant stress of 10 Pa.

3. A method of making-up a keratinous substrate comprising applying onto the substrate the composition of claim 1.

* * * * *